United States Patent
Mendes et al.

[11] Patent Number: 6,159,246
[45] Date of Patent: Dec. 12, 2000

[54] SURGICAL METHOD AND TOOL FOR REPAIRING A PATELLA OF THE KNEE JOINT

[76] Inventors: David Mendes; Ruth Beer, both of 8 Keller St., Haifa 34483, Israel

[21] Appl. No.: 08/837,290

[22] Filed: Apr. 11, 1997

Related U.S. Application Data

[63] Continuation-in-part of application No. 08/735,927, Oct. 24, 1996, Pat. No. 5,824,099, which is a continuation-in-part of application No. 08/375,085, Jan. 19, 1995, Pat. No. 5,580,353.

Foreign Application Priority Data

Apr. 19, 1994 [IL] Israel ....................................... 109344

[51] Int. Cl.[7] .............................. A61F 2/38; A61B 17/56
[52] U.S. Cl. .................................. 623/20; 606/80; 606/86
[58] Field of Search ................................. 623/16, 18, 20; 606/79, 80, 82, 86–89, 96, 97, 102

[56] References Cited

U.S. PATENT DOCUMENTS

| | | | |
|---|---|---|---|
| 5,129,907 | 7/1992 | Heldreth et al. | 606/88 |
| 5,129,908 | 7/1992 | Petersen | 606/88 |
| 5,520,692 | 5/1996 | Ferrante | 606/96 |
| 5,536,271 | 7/1996 | Daly et al. | 606/88 |
| 5,575,793 | 11/1996 | Carls et al. | 606/80 |
| 5,658,291 | 8/1997 | Techiera | 606/80 |
| 5,716,360 | 2/1998 | Baldwin et al. | 606/80 |
| 5,716,362 | 2/1998 | Treacy | 606/80 |

*Primary Examiner*—David J. Isabella

[57] ABSTRACT

A surgical method and device are provided which enable to prepare a natural patella for accepting a patella implant, while preserving a predetermined thickness of the natural patella. The device comprises: (a) a bone shaping element such as a reamer or a miller, including: (i) a rotatable bone shaping member having a lower edge; (ii) a shaft member having a scale including at least one marker; and (b) a guiding device for guiding the bone shaping element, including: (i) a patella holder for holding the natural patella; (ii) a pointer positioned at a constant distant from the patella holder for pointing at the marker, such that the distance between the pointer and the patella holder equals the sum of: the distance between the marker and the lower edge of the bone shaping member; and the preserved thickness of the natural patella. The method comprises: (a) holding the natural patella by means of a patella holder; (b) shaping the natural patella by means of a bone shaping element, the bone shaping element having: a marker; and a lower edge; (c) monitoring the shaping by means of a pointer, the distance between the pointer and the patella holder being equal to the sum of: (i) the distance between the marker and the lower edge; and (ii) the preserved thickness of the natural patella, such that when the marker merges with the pointer, a conclusion is made that the preserved thickness of the natural patella equals the predetermined value.

14 Claims, 4 Drawing Sheets

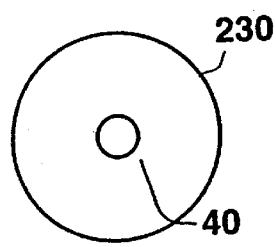
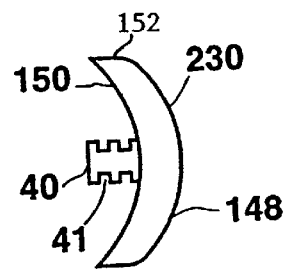
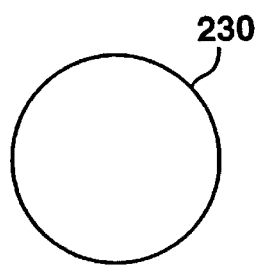
FIG. 4　　　FIG. 3　　　FIG. 5
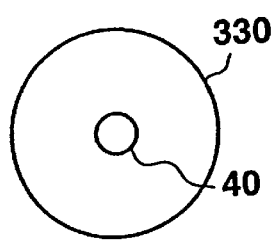
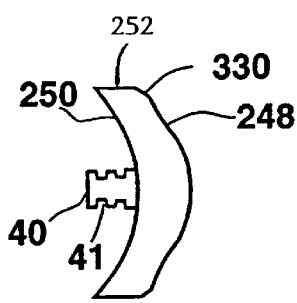
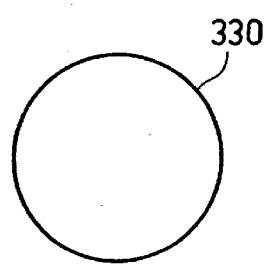
FIG. 7　　　FIG. 6　　　FIG. 8
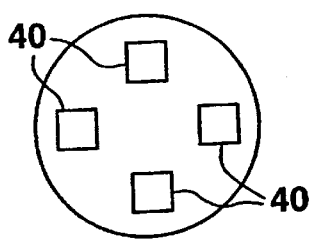
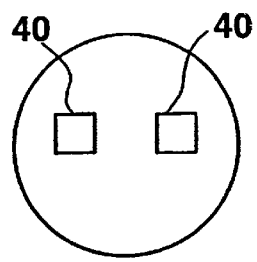
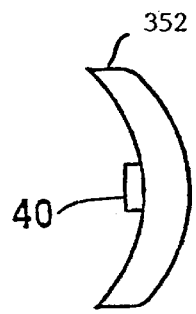
FIG. 10　　FIG. 9　　FIG. 11
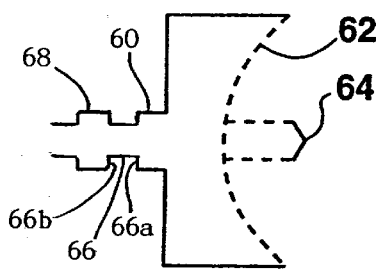
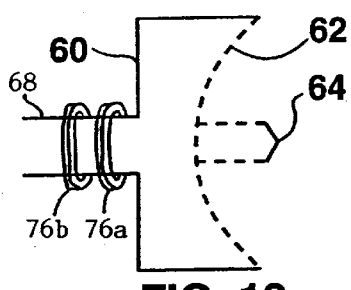
FIG. 12　　FIG. 13

SURGICAL METHOD AND TOOL FOR REPAIRING A PATELLA OF THE KNEE JOINT

This is a continuation in part of U.S. patent application Ser. No. 08/735,927, filed Oct. 24, 1996, now U.S. Pat. No. 5,824,099 which is a continuation in part of U.S. patent application Ser. No. 08/375,085, filed Jan. 19, 1995, now U.S. Pat. No. 5,580,353, issued Dec. 3, 1996.

FIELD AND BACKGROUND OF THE INVENTION

The present invention relates to a surgical method and tool for repairing a natural patella of the knee joint and, more particularly, to a surgical method and tool for reshaping a natural patella and fixing a patella implant to the remaining portion of a natural patella.

Joint replacement is becoming increasingly widespread. One of the most widely practiced joint replacement involves the knee joint. In many cases, the replacement of the knee joint with a prosthesis also involves the replacement of a portion of the patella with a prosthetic.

Partial replacement of the patella is widely used in the surgical replacement of a damaged portion of the knee joint. However, it is known that, in a significant percentage of the cases, the patella implant typically fails after five to fifteen years. One of the typically occurring failures is near or at the periphery of the circular or elliptical patella implant, where the thickness of the patella implant material, typically high molecular weight high density polyethylene (HDPE), is at its smallest. A failing patella could lead to significant pain in the patient and typically requires a second operation to replace the failed patella implant and often the entire prosthetic joint.

U.S. patent application Ser. No. 08/375,085 discloses a prosthetic patella implant adapted to structurally fit a remaining portion of the natural patella with maximal preserving of healthy natural tissue and minimal wear of the implant.

U.S. patent application Ser. No. 08/375,927 discloses a surgical method and tool for preparing a natural patella by removing a portion thereof to accept the patella implant described in U.S. patent application Ser. No. 08/375,085.

The present invention further relates to a surgical method and device for preparing a natural patella to accept a patella implant while preserving a predetermined thickness of the natural patella.

SUMMARY OF THE INVENTION

According to the present invention there is provided a method of repairing a natural patella, comprising the steps of: (a) preparing the natural patella by removing a portion thereof so as to leave a substantially convex remaining portion; and (b) fixing a patella implant onto the convex remaining portion of the natural patella, the patella implant including: an upper surface for sliding over the femoral articulating member; a substantially concave undersurface for fixation to the substantially convex remaining portion of the natural patella; and a circumferential facet.

According to further features in preferred embodiments of the invention described below, a method according to the present invention further includes the step of drilling at least one hole within the remaining portion of the natural patella for accepting at least one peg, the at least one peg being connected to the patella implant.

The diameter of the patella implant may be substantially equal to the diameter of the natural patella. Alternatively, the diameter of the patella implant may be substantially smaller than the diameter of the natural patella.

The circumferential facet of the patella implant may be cylindrical or conical in shape. A conical circumferential facet may be used for facilitating the attachment of the patella implant to the remaining portion of the natural patella by means of press fitting or other fixation techniques.

According to still further features of the invention described below, the surgical method is carried out using a reamer which includes a concave rotatable reaming member, and preferably one central bit.

Thus, according to the present invention there is further provided a reamer for use in preparing a natural patella to accept a patella implant having a substantially concave undersurface, comprising: a concave rotatable reaming member, the concavity of the reaming member being substantially equal to the concavity of the undersurface.

A reamer according to the present invention may further comprise a central bit protruding from the concave rotatable reaming member for drilling a hole in the natural patella and for guiding the reaming member to a predetermined portion of the natural patella.

Alternatively, a reamer according to the present invention may include a central bit having blunt end for guiding the reaming member through a pre-drilled hole in the natural patella.

The diameter of the reaming member may be substantially equal to or smaller than the diameter of the natural patella.

According to the present invention there is provided a design which will enable the manufacture of a HDPE patella implant with an overall thickness of not less than about 8 mm. This thickness is considered in the scientific literature as an optimal thickness for a high molecular weight high density polyethylene (HDPE) patella implant for use in an average person weighing 60–70 kg or more, for preventing high stresses within the material. Smaller thicknesses are to be used in smaller patients.

The use of the augmented minimum thickness eliminates one of the main causes of failure of patella implants and enhances the durability of the implant.

To provide the required optimal thickness of the patella implant, the natural patella is cut, reamed and trimmed, or alternatively milled in such a manner as to remove a total of up to about 8 mm or more from the natural bone and cartilage to leave a convex shape which complements the concave shape of the undersurface of the patella implant.

The concave undersurface of the patella implant fits the appropriately reamed remaining portion of the natural patella. The upper surface articulates with the articulating femoral member, typically a groove, and is shaped to fit the corresponding articulating portion of the femoral component of the total knee implant. When the articulating femoral member is a groove, the upper surface of the implant is typically substantially convex. Where the upper surface is convex the convexity of the upper surface and the concavity of the undersurface of a patella implant according to the present invention do not necessarily conform to each other and may be independently varied to accommodate the specific design of the femoral groove and the femoral condyles, or their equivalent, and the convexity of the prepared natural patella.

According to another embodiment, the remaining natural patella is shaped so as to preserve, rather than remove, a predetermined thickness of the natural patella.

Thus, the present invention provides a bone shaping device which enables to prepare a natural patella for accepting a patella implant, while preserving a predetermined thickness of the natural patella. The bone shaping device comprises: (a) a bone shaping element, including: (i) a rotatable bone shaping member having a lower edge; (ii) a shaft member having a scale including at least one marker; and (b) a guiding device for guiding the bone shaping member, including: (i) a patella holder for holding the natural patella; (ii) a pointer positioned at a constant distant from the patella holder for pointing at the marker, such that the distance between the pointer and the patella holder equals the sum of: the distance between the marker and the lower edge of the bone shaping member; and the preserved thickness of the natural patella.

Preferably, the bone shaping element is a reamer, and the rotatable bone shaping member is a reaming member. Alternatively, the bone shaping element is a miller, and the rotatable bone shaping member is a milling member.

The patella holder may feature a ring-like shape. Further, the patella holder may be saw-toothed.

The guiding device may further include: (a) a sleeve member for guiding the bone shaping element therein; and (b) a sleeve holder for attaching the sleeve member to the guiding device.

Further, the present invention provides a method for preparing a natural patella to accept a patella implant while preserving a predetermined thickness of the natural patella. The method comprises: (a) holding the natural patella by means of a patella holder; (b) shaping the natural patella by means of a bone shaping element, the bone shaping element having: a marker; and a lower edge; (c) monitoring the shaping by means of a pointer, the distance between the pointer and the patella holder being equal to the sum of: (i) the distance between the marker and the lower edge; and (ii) the preserved thickness of the natural patella, such that when the marker merges with the pointer, a conclusion is made that the preserved thickness of the natural patella equals the predetermined value.

The method may further comprise: guiding the bone shaping element within a sleeve member.

The present invention successfully addresses the shortcomings of the presently known configurations by providing a surgical method and tool for repairing a natural patella by reshaping the natural patella and fixing a patella implant to the remaining portion of the natural patella, such that the overall combination of patella implant and remaining natural patella features a maximal biomechanical stability. This is achieved by maximizing the volume of the remaining natural patella, minimizing the potential damage to necessary blood vessels at the periphery of the natural patella, conferring an optimal mechanical stability to the implant itself by limiting its minimal thickness to about 8 mm or alternatively about 6 mm, and providing complementary shapes to the implant and the remaining natural tissue.

Further, the present invention successfully addresses the shortcomings of the presently known configurations by providing a surgical method and tool wherein the bone shaping process is measured as a function of the preserved thickness of the natural patella rather than the removed thickness of the natural patella, thereby providing an identical common surgical procedure independent of the initial thickness of the remaining natural patella. Thus, method and tool according to the present invention enable to facilitate the surgical procedure and may eliminate the need to measure the initial thickness of the remaining natural patella, thereby saving surgery time.

BRIEF DESCRIPTION OF THE DRAWINGS

The invention is herein described, by way of example only, with reference to the accompanying drawings, wherein:

FIG. 3 is a cross sectional view of one embodiment of a patella implant according to the present invention;

FIG. 4 is a back view of the patella implant of FIG. 3;

FIG. 5 is a front view of the patella implant of FIG. 3;

FIG. 6 is a cross sectional view of another embodiment of a patella implant according to the present invention;

FIG. 7 is a back view of the patella implant of FIG. 6;

FIG. 8 is a front view of the patella implant of FIG. 6;

FIG. 9 is a back view of the patella implant showing a pair of fixation members;

FIG. 10 is a back view of the patella implant showing four fixation members;

FIG. 11 is a cross sectional view of another embodiment of a patella implant according to the present invention;

FIG. 12 is a cross sectional view of one embodiment of a bone shaping element which may be used to prepare a natural patella for acceptance of a patella implant according to the present invention;

FIG. 13 is a side view, partially in cross section, of a second embodiment of a bone shaping element according to the present invention.

DESCRIPTION OF THE PREFERRED EMBODIMENTS

The present invention is of a surgical method and tool for repairing a natural patella of the knee joint. Specifically, the present invention is of a surgical method and tool for reshaping a natural patella and fixing a patella implant to the remaining portion of a natural patella.

The principles and operation of a surgical method and tool according to the present invention may be better understood with reference to the drawings and the accompanying description.

Figure 1:
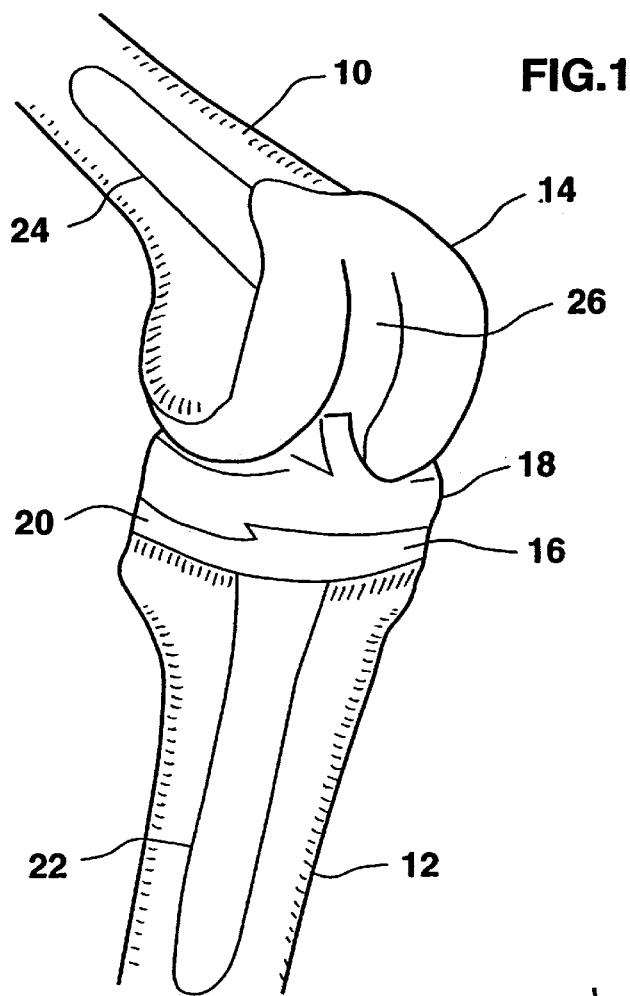
FIG. 1 is perspective view of a typically artificial knee joint.

Referring now to the drawings, FIG. 1 illustrates a typical knee joint prosthesis. The knee joint is formed between the lower end of the femur 10 and the upper end of the tibia 12. In a total knee replacement, the lower end of femur 10 is replaced with a femoral prosthetic component 14 while the upper end of tibia 12 is replaced with a tibial prosthetic component 16.

Tibial prosthetic component 16 is typically made up of a plastic upper plate 18 and a metal back 20. A tibial anchorage stem 22 connected to metal plate 18 is typically used to anchor tibial prosthetic component 16 into tibia 12. Tibial anchorage stem 22 may feature various lengths.

Femoral prosthetic component 14 is typically made of metal and is anchored into femur 10, preferably with a femoral anchorage stem 24. The face of femoral prosthetic component 14 which contacts tibial prosthetic component 16 is typically shaped to mimic the natural knee to include a groove 26. It is on groove 26, or its equivalent, that the patella slides, as can be best be seen in FIG. 2.

Figure 2:
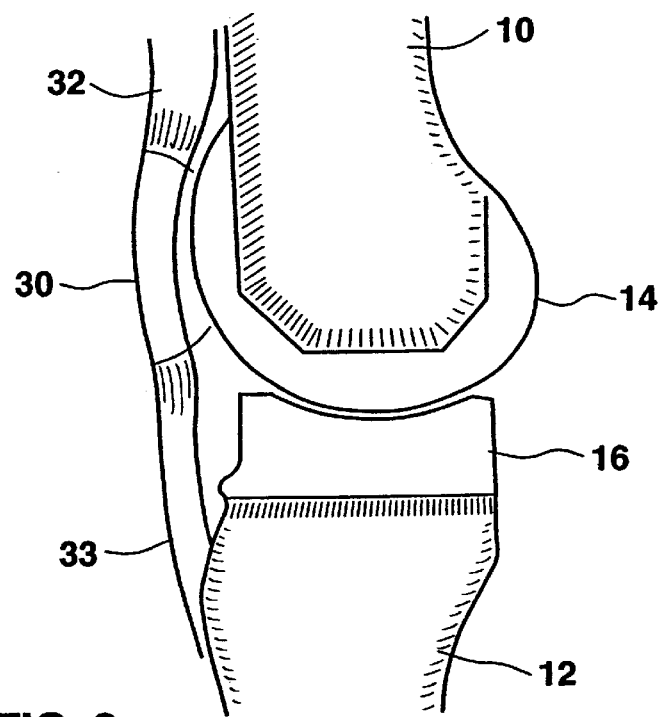
FIG. 2 is a side view of an artificial knee joint as in FIG. 1 showing the patella, quadriceps tendon and patella tendon.

FIG. 2 illustrates a total knee implant including the replacement of the articulating portion (the portion facing the knee) of the patella. As FIG. 2 illustrates, the patella (knee cap) 30 is a disc-shaped member which is connected to the quadriceps tendon 32 and to the patella tendon 33 and is slidable over the lower end of femur 10. The portion of patella 30 facing the knee (the patella implant) is typically, but not necessarily, convex and is dimensioned to slidably engage the corresponding portion of femoral prosthetic component 14, typically groove 26 and the femoral condyles (FIG. 1). The portion of patella 30 away from the knee (the remaining natural patella) is connected to quadriceps tendon 32 and patella tendon 33. Quadriceps tendon 32 is connected to the quadriceps muscle which is, in turn, attached to femur 10. Patella tendon 33 is connected to tibia 12. In this way patella 30 slides over the knee joint during flexion and extension of the joint. The presence of patella 30 facilitates the sliding of quadriceps tendon 32 and further enhances its mechanical efficiency.

To surgically repair a damaged patella what is done is to remove a portion of the articulating surface (the surface facing the knee joint) of the natural patella, leaving the connection between the natural patella and the muscle intact.

Once a portion of the patella has been removed, a prosthetic, or implant, may be fixed to the remaining portion of the natural patella by some suitable means. The implant is shaped to slidably fit within the groove, or its equivalent, of the corresponding natural or prosthetic lower end of the femur, depending on whether the natural lower femur is to remain or be replaced, respectively. Attachment of the implant to the natural patella may be effected with adhesives, cements or other bonding materials and/or through use of pegs, as described in more detail below. U.S. patent application Ser. No. 08/375,085 discloses a prosthetic patella implant adapted to structurally fit a remaining portion of the natural patella with maximal preserving of healthy natural tissue and minimal wear of the implant.

As shown in FIGS. 3 and 6, the patella implant, 230 or 330, features a substantially convex upper surface, 148 or 248, for sliding over a femoral articulating member; a substantially concave undersurface, 150 or 250, for fixation to a convexly sectioned natural patella; and a circumferential facet, 152 or 252.

When using a polyethylene patella implant, the distance between the upper surface and the undersurface is at least 8 mm or 6 mm for small patients, so as to confer maximal mechanical integrity to the patella implant.

Undersurface, 150 or 250, preferably features a substantially concave shape so as to allow maximal preserving of remaining natural bone tissue. However, undersurface, 150 or 250, may feature a flattened central portion or any other shape which enhances the bonding of the implant to the natural patella.

Figure 15:
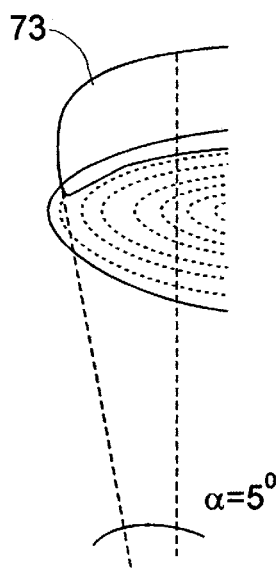
FIGS. 15 and 16 illustrate another embodiment of a method according to the present invention.
Figure 16:
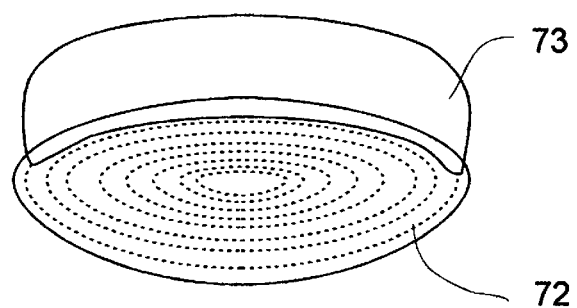

Circumferential facet, 152 or 252, is specifically designed so as to minimize potential damage to necessary blood vessels at the periphery of the natural patella. As shown in FIGS. 3 and 6, circumferential facet, 152 or 252, may feature a cylindrical shape. However, as shown in FIG. 11, circumferential facet 352 may feature a conical shape. A conical circumferential facet may be used for facilitating the attachment of the patella implant to the remaining portion of the natural patella by means of press fitting or other fixation techniques (FIGS. 15 and 16).

As shown in FIGS. 3–11, the patella implant may include one or more pegs 40. Pegs 40 may be of any suitable size. Thus, pegs 40 may extend beyond the lower edge of the circumferential facet (FIGS. 3 and 6). Alternatively, pegs 40 may not extend beyond the lower edge of the circumferential facet (FIG. 11).

Preferably, pegs 40 are formed with circumferential depressions 41 (FIGS. 3 and 6) which improve the bonding and anchorage of the patella implant to the natural bone tissue by providing enhanced friction and further providing space in which cement and the like can accumulate.

The present invention provides a surgical method for repairing a natural patella by reshaping the natural patella and fixing a patella implant to the remaining portion of the natural patella, such that the overall combination of patella implant and remaining natural tissue has maximal biomechanical stability.

Further, the present invention provides a surgical tool for preparing a remaining natural patella to accept the patella implant.

A method according to the present invention includes the step of preparing a natural patella to accept a patella implant having a substantially concave undersurface, such that there is maximal preservation of natural bone tissue and minimal damage to necessary blood vessels at the periphery of the natural patella.

Thus, the natural patella is surgically prepared to preferably adopt a substantially convex shape complementary to the undersurface of the patella implant.

A method according to the present invention may further include the step of drilling at least one hole within the remaining portion of the natural patella for accepting at least one peg, the at least one peg being connected to the patella implant as shown in FIGS. 3–11.

The surgical preparation of the natural patella is preferably carried out using a special surgical tool which cuts the bony patella to precisely the desired shape with minimal interference of its blood supply from the surrounding tissues.

The special tool is a concave surgical bone shaping element 60 such as a reamer or a miller (FIG. 12) which can be powered electrically, pneumatically, mechanically, manually, and the like. Bone shaping element 60 can be used to remove an appropriate amount of bone in order to create a convex surface of cortical and/or cancellous bone of the bony patella which accurately fits the concave undersurface of a patella implant according to the present invention.

Bone shaping element 60 includes a concave rotatable bone shaping member 62 whose concavity is substantially equal to the concavity of the patella implant undersurface. Bone shaping member 62 may be a reaming member. Alternatively, bone shaping member 62 may be a milling member. Preferably, bone shaping element 60 further includes a bit 64 which protrudes from concave rotatable bone shaping member 62 and which is used to simultaneously drill a hole in the natural patella which will accommodate a single central peg extending from the undersurface of the implant.

Bit 64 is also used as a guide means for guiding rotatable bone shaping member 62 to a predetermined portion of the natural patella so that as bone shaping element 60 is moved the natural patella is shaped to match the undersurface of the patella implant.

Alternatively, bit 64 may feature a blunt end and may be used for guiding bone shaping member 62 through a substantially central hole pre-drilled in the natural patella.

As shown in FIG. 12, bone shaping element 60 may feature a shaft member 68. Shaft member 68 may feature a circumferential depression 66 having two edges, 66a and 66b, for accepting an external rod (not shown) therein, the rod being connected to an external guiding device. Thus, as bone shaping element 60 is moved, the external rod is moved along depression 66 until it is blocked by edge 66b. The extent of movement of bone shaping element 60 is thus limited by the dimensions of the external rod and depression 66. Such configuration is preferably used for removing a predetermined thickness of the remaining natural patella, the predetermined thickness being preferably equal to the distance between edges 66a and 66b.

Alternatively, as shown in FIG. 13, bone shaping element 60 may include two circumferential extensions, 76a and 76b, the extensions being connected to shaft member 68. Thus, as bone shaping element 60 is moved, the external rod is moved between extensions 76a and 76b until it is blocked by extension 76b. The extent of movement of bone shaping element 60 is thus limited by the dimensions of the external rod and the distance between extensions 76a and 76b.

Circumferential extensions 76a and 76b may be movable along shaft member 68, such that the specific location of extensions 76a and 76b and the distance between the extensions may be adapted to a specific patient.

Rotatable bone shaping member 62 may feature a flattened central portion or any other shape substantially complementary to the undersurface of the patella implant. Further, bone shaping member 62 may feature any shape which provides enhanced bonding between the natural patella and the undersurface of the patella implant.

Figure 14:
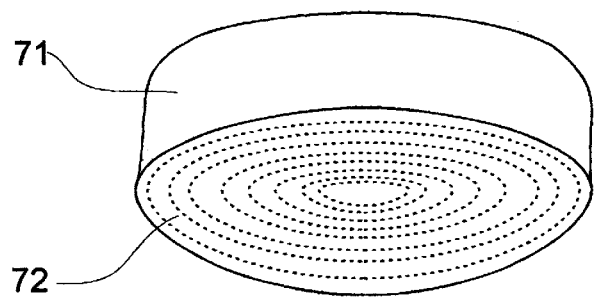
FIG. 14 illustrates one embodiment of a method according to the present invention.

Rotatable bone shaping member 62 may feature any suitable diameter. The diameter of bone shaping member 62 may approximately correspond to the diameter of the natural patella. Thus, as shown in FIG. 14, the natural patella 72 may be shaped using bone shaping element 60 so as to accept a patella implant of a substantially equal diameter.

Alternatively, the diameter of bone shaping member 62 may be smaller than the diameter of the natural patella. Thus, as shown in FIGS. 15 and 16, the natural patella 72 may be shaped using bone shaping element 60 so as to accept a patella implant 73 of a substantially smaller diameter. Such configuration makes it possible to partly intrude patella implant 73 into the natural patella.

Preferably, the patella implant features a cylindrical circumferential facet (FIGS. 3, 6 and 13) or a conical circumferential facet (FIGS. 11, 15 and 16). When using a conical circumferential facet, the angle of the cone is preferably about 5° (FIG. 15). A conical circumferential facet may be used for facilitating the attachment of the patella implant to the remaining portion of the natural patella by means of press fitting or other fixation techniques.

Preferably, fixation of the prosthetic patella implant to the natural patella is further effected by means of a bonding material or other chemical, physical or biological adhesives and by biological reactions, such as bone ingrowth into the surface, preferably using the pegs which fit into their respective holes in the prepared bone surface.

When using a patella implant with a plurality of pegs 40, their respective holes may be drilled independently by using a conventional drill, following the step of reshaping the natural patella by bone shaping element 60.

According to the present invention there are further provided method and device for preparing a natural patella to accept a patella implant while reserving a predetermined thickness of the natural patella.

Figure 17:
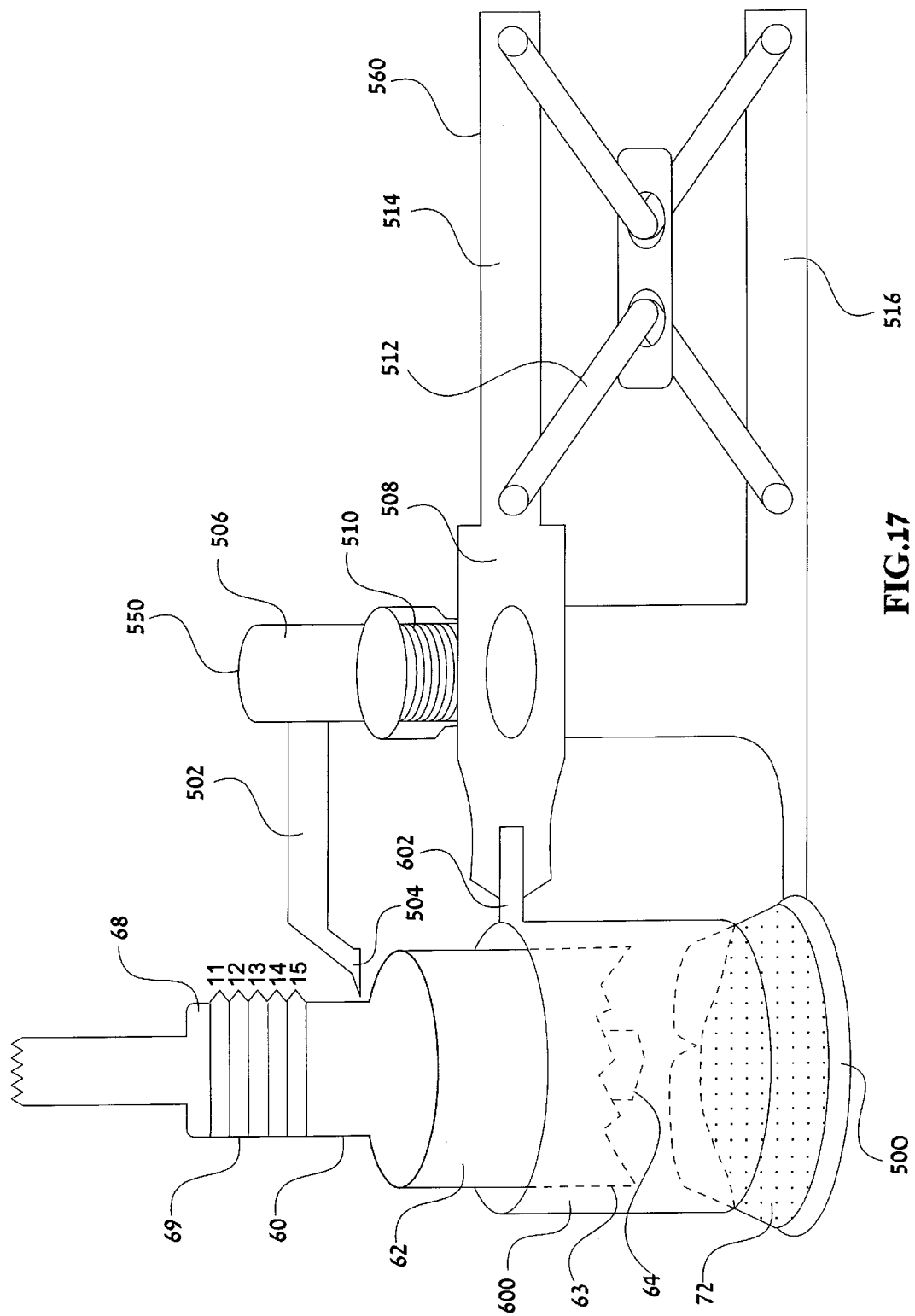
FIG. 17 is a schematic illustration of yet another embodiment of method and device according to the present invention.

As shown in FIG. 17, a bone shaping device according to the present invention preferably includes a guiding device 550 and a bone shaping element 60. Guiding device 550 preferably includes a clamp 560 having an upper rod 514, a lower rod 516, and a perpendicular rod 506. Upper rod 514 is preferably connected to or made as an integral part of a sleeve holder 508 for holding a sleeve member 600. Lower rod 516 is preferably connected to or made as an integral part of a patella holder 500. Upper rod 514 and lower rod 516 are preferably inter-connected by means of a double-action axes system 512 for keeping rods 514 and 516 parallel to each other as sleeve holder 508 slides over perpendicular rod 506, thereby constantly keeping sleeve member 600 perpendicular to the cortical surface of patella 72. Preferably, a screwing element or a string-like element 510 is used so as to determine an upper limit to sleeve holder 508, thereby determining the positioning of sleeve member 600 over patella 72.

Patella holder 500 preferably features a ring-like shape, and is preferably saw-toothed so as to tightly hold patella 72. Sleeve 600 preferably features a cylindrical shape and has an internal diameter which approximately equals the external diameter of bone shaping member 62. Further, sleeve 600 preferably features an extension 602 for holding by sleeve holder 508.

Clamp 560 preferably includes a scaling rod 502 having a pointer 504 for indicating the position of bone shaping element 60 with relation to the desired final position. Accordingly, bone shaping element 60 preferably includes a scale 69 having markers (denoted as 11–15) for indicating the preserved thickness of patella 72 during the bone shaping process. When pointer 504 merges with a distinct marker, a conclusion is made that the preserved thickness of the patella 72 has reached the value indicated by the marker.

The principle underlying the operation of the described invention is as follows: the distance between pointer 504 and patella holder 500 is preferably constant, and equals the sum of: (a) the current preserved thickness of patella 72; and (b) the distance between the lower edge 63 of bone shaping element 60 and the specific marker on scale 69 currently pointed by pointer 504. Therefore, each marker on scale 69 pointed by pointer 504 denotes a specific preserved thickness of patella 72, the preserved thickness being equal to the difference between: (a) the pointer 504 and patella holder 500; and (b) the distance between the lower edge 63 of bone shaping element 60 and the specific marker.

According to another configuration (not shown), bone shaping element 60 includes a circumferential extension for blocking pointer 504 as it reaches a desired marker on scale 69.

Preferably, the desired preserved thickness of patella 72 is determined according to the specific dimensions of the treated patient. Preferably, the overall thickness of the preserved portion of the natural patella and the implant should be approximately equal to the thickness of a healthy natural patella. Thus, when treating an average patient, the preserved thickness of the natural patella following reaming should be about 13 mm. For larger patients, the preserved thickness should be about 14–15 mm. For smaller patients, the preserved thickness should be about 11–12 mm.

When using a bone shaping device according to the present invention for surgically treating an average patient, patella holder 500 is placed over patella 72 so as to tightly hold the bony portion of the natural patella. Sleeve holder 508 is then moved along perpendicular rod 506 so as to securely locate sleeve member 600 over patella 72. During the bone shaping process, bone shaping element 60 is guided within sleeve member 600.

When the marker on scale 69 denoted as "13" merges with pointer 504, a conclusion is made that the currently preserved thickness of patella 72 is 13 mm, and the bone shaping process is stopped.

While the invention has been described with respect to a limited number of embodiments, it will be appreciated that many variations, modifications and other applications of the invention may be made.

What is claimed is:

1. A bone shaping device for preparing a natural patella to accept a patella implant while preserving a predetermined thickness of the natural patella, comprising:
   (a) a bone shaping element, including:
      (i) a rotatable bone shaping member having a lower edge;
      (ii) a shaft member having a scale including at least one marker being connected said rotatable bone shaping member; and
   (b) a guiding device for guiding said bone shaping element, including a construction holding:
      (i) a patella holder for holding the natural patella;
      (ii) a pointer positioned at a constant distant from said patella holder for pointing at said marker,
   such that the distance between said pointer and said patella holder equals the sum of: the distance between said marker and said lower edge; and the preserved thickness of the natural patella.

2. The device of claim 1, wherein said bone shaping element is a reamer.

3. The device of claim 1, wherein said bone shaping element is a miller.

4. The device of claim 1, wherein said patella holder includes a ring-like shape.

5. The device of claim 1, wherein said patella holder is a ring shaped surface having a tooth configuration.

6. The device of claim 1, wherein said guiding device further includes:
   (a) a hollow sleeve member for guiding said bone shaping element therein; and
   (b) a sleeve holder for attaching said hollow sleeve member to said guiding device.

7. The device of claim 1, wherein said patella holder is connected to a first handle of a clamp and said sleeve holder is connected to a second handle of said clamp.

8. The device of claim 1, wherein said shaft member includes an extension connected to said marker.

9. A method for preparing a natural patella to accept a patella implant while preserving a predetermined thickness of the natural patella, comprising the steps of:
   (a) holding a natural patella by a patella holder;
   (b) shaping the natural patella by a bone shaping element, the bone shaping element including:
      (i) a rotatable bone shaping member having a lower edge;
      (ii) a shaft member having a scale including at least one marker being connect rotatable bone shaped numbers
   (c) monitoring said shaping by a pointer, the distance between said pointer and said patella holder being equal to the sum of:
      (i) the distance between said marker and said lower edge; and
      (ii) the preserved thickness of the natural patella,
   such that when said marker merges with said pointer, a conclusion is made that the preserved thickness of the natural patella equals the predetermined value.

10. The method of claim 9, wherein said bone shaping element is a reamer.

11. The method of claim 9, wherein said bone shaping element is a miller.

12. The method of claim 9, wherein said patella holder include a ring-like shape.

13. The method of claim 9, wherein said patella holder is a ring shaped with a surface having a saw tooth configuration.

14. The method of claim 9, further comprising the step of: guiding said bone shaping element within a hollow sleeve member.

* * * * *